United States Patent [19]

Fukutani et al.

[11] 4,083,725
[45] Apr. 11, 1978

[54] PHOTOSENSITIVE COMPOSITION

[75] Inventors: Hideo Fukutani, Tokyo; Konoe Miura, Kanagawa; Chihiro Eguchi, Kanagawa; Yoshihiro Takahashi, Kanagawa; Kazuo Torige, Yokohama, all of Japan

[73] Assignee: Mitsubishi Chemical Industries Ltd., Tokyo, Japan

[21] Appl. No.: 678,115

[22] Filed: Apr. 19, 1976

Related U.S. Application Data

[63] Continuation-in-part of Ser. No. 475,895, Jun. 3, 1974, abandoned.

[30] Foreign Application Priority Data

Jun. 2, 1973 Japan .................................. 48-62144

[51] Int. Cl.$^2$ .......................... G03C 1/68; C08F 8/18; C08F 8/34
[52] U.S. Cl. .............................. 96/115 R; 204/159.18
[58] Field of Search ................ 96/115 R; 204/159.18; 269/364

[56] References Cited

U.S. PATENT DOCUMENTS

| 2,034,629 | 3/1936 | Moser et al. | 260/364 |
|---|---|---|---|
| 2,059,647 | 11/1936 | Perkins | 260/364 |
| 2,418,318 | 4/1947 | Scalera | 260/364 |
| 2,531,465 | 11/1950 | Randall et al. | 260/364 |
| 2,670,285 | 2/1954 | Minsk et al. | 96/115 R |
| 3,817,876 | 6/1974 | Fukutani et al. | 96/115 R |
| 3,827,956 | 8/1974 | McGinniss | 264/159.23 |
| 3,914,128 | 10/1975 | Scheiber et al. | 204/115 R |
| 3,915,824 | 10/1975 | McGinniss | 96/115 X |

*Primary Examiner*—Jack P. Brammer
*Attorney, Agent, or Firm*—Oblon, Fisher, Spivak, McClelland & Maier

[57] ABSTRACT

A photosensitive composition is prepared from a mixture of a cinnamic acid photosensitive resin and a halogen-substituted benzanthrone sensitizer.

5 Claims, No Drawings

PHOTOSENSITIVE COMPOSITION

CROSS-REFERENCE TO RELATED APPLICATIONS

This application is a continuation-in-part of application Ser. No. 475,895 filed June 3, 1974, now abandoned.

BACKGROUND OF THE INVENTION

1. Field of the Invention

The present invention relates to a sensitizer for a cinnamic acid photosensitive resin, and to a photosensitive composition thereof.

2. Description of the Prior Art

Various polymers containing the cinnamic acid radical prepared by polymerization reactions of cinnamic acid or cinnamic acid derivatives with other polymers have been proposed for use as photosensitive resins in various fields. In general, these photosensitive polymers have low photosensitivity. To improve the photosensitivity lower molecular weight sensitizer compounds have been added. Recently, increased sensitivity has been required for precise and high quality applications of cinnamic acid photosensitive resins. Spectral sensitization, that is expanded sensitive wavelengths, is insufficient, and improved sensitivity at any specific wavelength is required. For example, the photoresists used for preparation of IC, LSI and masks in the semiconductor field, are exposed by a projection printing system. In the system, a g-line (4358 A) is generally employed because of optical aberration. Accordingly, in this system, an increased sensitivity to the g-line is required. Sufficient increase of sensitivity is impossible with known sensitizers. A need exists therefore for a cinnamic acid photosensitive resin with high sensitivity.

SUMMARY OF THE INVENTION

Accordingly, one object of the present invention is to provide a sensitizer for a cinnamic acid photosensitive resin with particular sensitivity when exposed to the g-line.

Another object of the invention is to provide a photosensitive composition which has high sensitivity to the g-line.

These and other objects of the present invention as will hereinafter become more readily understood can be attained by incorporating a halogen substituted benzanthrone (hydrogen atom of benzanthrone substituted with halogen) sensitizer into a cinnamic acid photosensitive resin. This composition imparts excellent sensitization to the cinnamic acid photosensitive resins, especially under exposure to the g-line.

DETAILED DESCRIPTION OF THE PREFERRED EMBODIMENTS

Suitable sensitizers of the invention include benzanthrone derivatives substituted with one or more halogen atoms of chlorine, or fluorine.

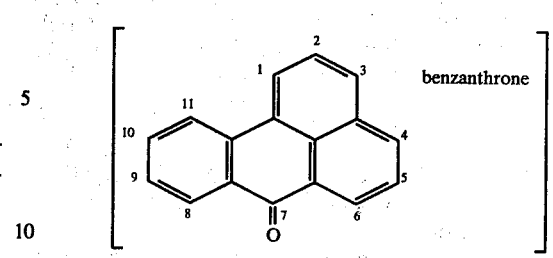

Suitable benzanthrone derivatives include monohalobenzanthrones, such as 3-chlorobenzanthrone, 3-fluorobenzanthrone, and 9-chlorobenzanthrone; and dihalobenzanthrones, such as 3, 4-dichlorobenzanthrone, 3, 9-dichlorobenzanthrone, 3, 11-dichlorobenzanthrone, 6, 11-dichlorobenzanthrone, 3, 6-difluorobenzanthrone, 6, 11-difluorobenzanthrone and 8, 11-difluorobenzanthrone.

Suitable cinnamic acid photosensitive polymers which are combined with the sensitizer of the invention include polymers containing the cinnamic acid group or a derivative of cinnamic acid.

The preferred photosensitive polymers have the following units in the molecule

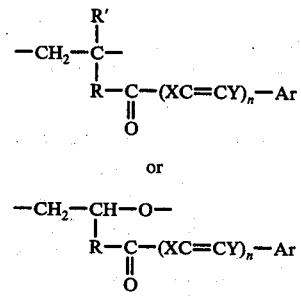

wherein R represents an oxygen atom or a hydrocarbon moiety containing an oxygen or sulfur atom; R' represents hydrogen or a lower alkyl group; and X and Y are the same or different and represent hydrogen, a halogen atom, cyano group or nitro group; Ar represents an aryl group which may be substituted; and $n$ represents the intergers 1 or 2.

Suitable photosensitive polymers include vinyl polymers prepared by reacting cinnamic acid or a derivative thereof with polymers containing the hydroxy, chloromethyl or acetyl group, such as polyvinyl cinnamate, poly (vinyl m-nitro-cinnamate), poly(vinyl α-cyanocinnamate), poly(vinyl α-nitro -cinnamate), poly(vinyl β-nitro-cinnamate), poly(vinyl α-chloro-cinnamate), poly(vinyl β-chloro-cinnamate), poly(vinyl cinnamylidene acetate), polyvinyloxyethyl cinnamate, polyvinylthioethyl cinnamate, poly(2-cinnamolyloxyethyl acrylate), poly(2-cinnamoyloxyethyl methacrylate), poly(vinyl cinnamoyloxyacetate), poly(p-cinnamoyloxyvinylbenzene), poly(p-cinnamoylstyrene), or the like; or copolymers of the monomer and another comonomer; and oxirane ring opened polymers such as polyglycidyl cinnamate, poly(glycidyl p-nitrocinnamate), poly(glycidyl α-cyanocinnamate), poly(glycidyl cinnamylidene acetate) or the like. Suitable polymers containing photosensitive groups which are produced by reacting a polymer containing haloalkyl group side chains with a salt of a carboxylic acid containing photosensitive groups in a dipolar aprotic solvent may also be used. For example, the polymers can be produced by reacting polychloroethylvinyl ether, polyvinyl chloroacetate, poly(β-chloroethyl acrylate), polyeprichlorohydrin, or polyepibromohydrin with cinnamic acid or a derivative thereof. Suitable polymers can also be prepared by cationic polymerization of vinyl ethers such as poly(vinyloxyethyl cinnamate), or the like. The quantity of the sensitizer of the invention may vary and is preferably 0.01 – 10% by weight of the cinnamic acid photosensitive polymer.

The photosensitive resin and the sensitizer are used by dissolving the components in a solvent. Suitable solvents include the known solvents. e.g. acetone, toluene, xylene, methylcellosolve acetate or the like. The solvents also include chlorobenzene, bromobenzene, 4-methoxy-4-methylpentanone-2, or the like. Conventional sensitizers such as aromatic nitro compounds or ketones may also be added, as well as stabilizers, such as hydroquinone, tert-butyl catechol or the like; plasticizers, such as triacetin, triethyleneglycol dipropionate or the like; dyestuffs; or pigments, depending upon the desired properties. In accordance with the employment of a sensitizer of the invention, the sensitivity of cinnamic acid photosensitive polymers is improved. Most importantly, the sensitivity under exposure to the g-line is remarkably improved.

Having generally described the invention, a further understanding can be obtained by certain specific examples which are provided herein for purposes of illustration only and are not intended to be limiting in any manner.

Preparation 1—Cinnamic Acid Photosensitive Polymer

A 10 g amount of polyepichlorohydrin having a reduced specific viscosity $\eta SP/C = 0.97(0.2$ g/dl benzene sol. at 30° C) was dissolved in 342 ml of dimethylformamide, and 20.8 of cinnamic acid and 21.4 g of 1,8-diazabicyclo [5,4,0] undecene-7 were added. A homogenous solution was formed. The reaction was conducted at 85° C for 9 hours with stirring in an argon atmosphere. The reaction mixture was then poured into about 1.5 of methanol to precipitate the white rubberlike polymer. The resulting polymer had units of the following formula:

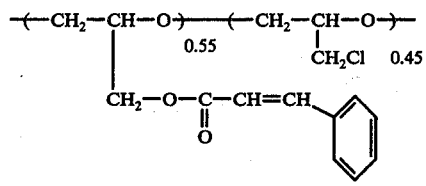

Preparation 2—Sensitizer

A 9.7 amount of 1, 5-dichloroanthraquinone was dissolved in 75.5 ml of conc. sulfuric acid. 5.5ml of water was added dropwise to the solution. 4.8 g of copper powder was added to the solution during 1 hour and the mixture was stirred at 40° C for 2.5 hours. A mixture of 9.6 g of glycerine and 9.6 ml of water was added to the mixture to raise the temperature to 75° C. The mixture was further heated to 110° C at a rate of 1° C per 3 minutes, and the reaction was conducted at 110° C for 1.5 hours. 400 ml of the reaction mixture was poured into water to obtain a yellowish green powder. The product was recrystallized from o-dichlorobenzene and chlorobenzene to obtain yellow needle crystals (mp 180° C). According to the analysis, the product was 6, 11-dichlorobenzanthrone.

Preparation 3—Sensitizer

Monochlorobenzanthrone was prepared from 2-chloroanthraquinone in accordance with preparation 2.

Preparation 4—Sensitizer

A 10g amount of benzanthrone was dissolved in a solvent mixture of 100g acetic acid and 100 g of water. 6 g of potassium chlorate was added to the solution and the mixture was heated and stirred at 90°–95° C for 2 hours. 12 g of conc. hydrochloric acid was added dropwise to the mixture during 1 hour and 20 minutes. After the addition, the mixture was stirred for 1 hour to complete the reaction. The reaction mixture was cooled, filtered, washed with water and dried. The product was recrystallized from chlorobenzene to obtain 3-chlorobenzanthrone having a melting point of 179°–190° C (orange needle crystals).

EXAMPLE 1

An 8.5 g amount of the photosensitive polymer prepared as described in Preparation 1 was dissolved in 100 ml of 4-methoxy-4-methylpentanone-2. 0.8 g of 6,11-dichlorobenzanthrone prepared as described in Preparation 2 was added to the solution to prepare a photosensitive solution. The photosensitive solution was coated with a spinner on to a glass plate coated with vapor deposited chromium (50 × 50 mm). The coated plate was prebaked at 80° C for 15 minutes. The coated plate was contacted with the Steps tablet No. 2 (Kodak Co.) and was exposed for 10 seconds at a 30 cm distance from the source of a high pressure mercury lamp (manufactured by Ushio Denki K. K. under the trade name of Unipalse 3KW), to the g-line passed through a colored glass filter (manufacture by Toshiba K. K. under the trade name of V-Y43 and VC1A). A solvent mixture of xylene and cyclohexanone (2 : 1 by volume) was sprayed on to the exposed coated plate as a developing solution. The relative sensitivity (S) was calculated by the following equation (1) from the insolubilized steps:

$$S = \frac{k \cdot \text{antilog } D}{I_o \cdot t} \quad (1)$$

wherein the constant $k$ was chosen to be 100 times the relative sensitivity S of benzanthrone; D designates the optical density of the step tablets for the insolubilized limit steps; $t$ designates exposure time (seconds); $I_o$ designates optical intensity (relative value) on the surface of the sample. The relative sensitivity S of the sample was 280.

EXAMPLE 2

In accordance with Example 1, 0.7 g of monochlorobenzanthrone prepared as described in Preparation 3 was used as the sensitizer, and the relative sensitivity S of the sample was measured as 140.

EXAMPLE 3

In accordance with Example 1, 0.7 g of 3-chlorobenzanthrone prepared as described in Preparation 4 was used as the sensitizer, and the relative sensitivity S of the sample was measured as 140. The relative sensitivities of the samples were determined using the known sensitizers benzanthrone, 5-nitroacenaphthene and 1, 2-benzanthraquinone and the sensitizers of the invention. The results are shown in Table 1.

TABLE 1

| Sensitizer | Relative Sensitivity |
| --- | --- |
| 6,11-dichlorobenzanthrone | 280 |
| monochlorobenzanthrone | 140 |
| 3-chlorobenzanthrone | 140 |
| benzanthrone | 100 |
| 5-nitroacenaphthene | 40 |
| 1,2-benzanthraquinone | 25 |

EXAMPLE 4—Preparation of 3-bromobenzanthrone

A solution of 11.2 g of bromine in 20.5 g of acetic acid was added dropwise to a mixture of 11.5 g of benzanthrone, 184 g of acetic acid and 23 g of water with stirring. The total mixture was heated with stirring to 100° C for 5.5 hours. The precipitated crystals were filtered and washed with water and dried. The product was recrystallized from a mixture of 88.3 g of chlorobenzene and 6.3 g of methanol whereby 10.52 g of 3-bromobenzanthrone were obtained.

EXAMPLE 5—Preparation of 3-fluorobenzanthrone

A 1 g amount of 3-aminobenzanthrone was dissolved in a mixture of 5 ml of conc. hydrochloric acid and 10 ml of water. A 2.3 g amount of $NaBF_4$ was added to the resulting solution and 1.3 g of $NaNO_2$ in 5 ml of water was added to the solution cooled with ice. The mixture was stirred for 45 minutes and was filtered with suction to obtain a yellowish brown solid. The product was heat-decomposed by heating at about 155° C for 2 hours and was extracted with acetic acid and treated with activated carbon whereby 3-fluorobenzanthrone was obtained.

EXAMPLE 6—Preparation of 3-iodobenzanthrone

A 2 g amount of 3-aminobenzanthrone was dissolved in a mixture of 60 g of ice, 60 g of water and 15 ml of conc-sulfuric acid to obtain a solution. A solution of 2g of $NaNO_2$ in 10 ml of water was gradually added to the solution. The mixture was stirred to react the components in order to obtain a diazonium salt of benzanthrone. The diazonium salt was gradually added to a solution of 5 g of KI in 10 ml of water and a small amount of copper powder was added to the solution. The mixture was heated to 80° C and reacted at 80° C for 1 hour and further at about 110° C for 1 hour. The resulting solid was extracted with hot benzene and treated with activated carbon and recrystallized from benzene whereby 3-iodobenzanthrone was obtained.

EXAMPLE 7

The procedure of Example 1 was repeated 3 times except that 0.8 g of 3-bromobenzanthrone (Example 4), 0.7 g of 3-fluorobenzanthrone (Example 5) or 0.9 of of 3-iodobenzanthrone (Example 6) was used in the composition to achieve a measure of the relative sensitivity S of each sensitizer. The results obtained are as follows:

| Sensitizer | Relative Sensitivity |
| --- | --- |
| 3-bromobenzanthrone | 25 |
| 3-fluorobenzanthrone | 130 |
| 3-iodobenzanthrone | 0 |
| benzanthrone | 100 |

EXAMPLE 8

The photosensitive solution prepared as described in Example 1 was coated with a spinner (3000 rpm) on to a silicon wafer covered with an oxidized membrane 1 $\mu$ thick. The coated silicon wafer was exposed for 3 minutes to the g-line, passed through a mask, for the preparation of an integrated circuit by a projection type printer (Canon K.K. PPC-210). The exposed sample was developed with a solvent mixture of xylene and cyclohaxanone (2 : 1 by volume), and then was postbaked at 170° C for 20 minutes. The resulting sample was treated with a fluoric acid etching solution at 25° C for 6 minutes to obtain a sharp pattern.

EXAMPLE 9

The photosensitive solution prepared as described in Example 1 was coated with a spinner onto a smooth glass plate coated with vapor deposited chromium (50 × 50 mm). The coated plate was prebaked at 70° C for 20 minutes. The coated plate was exposed by a projection printer to print a fine pattern having lines 1 – 50 $\mu$ thick. A solvent mixture of xylene and cyclohexanone (2 : 1 by volume) was applied onto the exposed coated plate as a developing solution. The plate was then postbaked at 170° C for 20 minutes. The resulting plate was etched with an ammonium ceric nitrateperchloric acid etching solution at 21° C for 60 seconds to obtain a sharp pattern. The product could be used as a hard mask for the preparation of a semi-conductor.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A photosensitive composition, which consists essentially of:
 a photosensitive resin containing pendant cinnamic acid radicals, and from 0.01 – 10% by weight of a sensitizer of a nuclear-chloro substituted benzanthrone or a nuclear-fluoro substituted benzanthrone based on the photosensitive resin.

2. The photosensitive composition of claim 1, wherein the nuclear-chloro substituted benzanthrone sensitizer is a monochlorobenzanthrone or dichlorobenzanthrone.

3. The photosensitive composition of claim 2, wherein said monochlorobenzanthrone is 3-chlorobenzanthrone or 9-chlorobenzanthrone.

4. The photosensitive composition of claim 2, wherein said dichlorobenzanthrone is 3,4-dichlorobenzanthrone or 6,11-dichlorobenzanthrone.

5. The photosensitive composition of claim 1, wherein said nuclear-fluoro substituted benzanthrone is 3-fluorobenzanthrone, 3,6-difluorobenzanthrone, 6,11-difluorobenzanthrone or 8,11-difluorobenzanthrone.

* * * * *